United States Patent [19]

Mazuel

[11] Patent Number: 4,996,197

[45] Date of Patent: Feb. 26, 1991

[54] PHARMACEUTICAL AND/OR COSMETIC COMPOSITION FOR LOCAL USE CONTAINING RHAMSAN GUM

[75] Inventor: Claude Mazuel, Riom, France

[73] Assignee: Laboratoires Merck Sharp & Dohme-Chibret, Paris, France

[21] Appl. No.: 223,572

[22] Filed: Jul. 25, 1988

[30] Foreign Application Priority Data

Jul. 20, 1987 [FR] France ............................. 87 10211

[51] Int. Cl.$^5$ ........................................... A61K 31/715
[52] U.S. Cl. ..................................... 514/54; 536/114; 536/123; 514/777; 514/844; 514/912; 514/913; 514/914; 514/915; 514/944
[58] Field of Search ................. 514/54, 912, 913, 914, 514/915, 844, 944, 777; 536/114, 123

[56] References Cited

U.S. PATENT DOCUMENTS

| | | | |
|---|---|---|---|
| 4,136,173 | 1/1979 | Pramoda et al. ...................... | 514/15 |
| 4,304,906 | 12/1981 | Kang et al. ......................... | 536/123 |
| 4,401,760 | 8/1983 | Peik et al. ........................... | 536/123 |
| 4,792,415 | 12/1988 | Colegrove ........................... | 536/114 |
| 4,861,760 | 8/1989 | Mazuel et al. ...................... | 536/114 |
| 4,874,423 | 10/1989 | Colegrove et al. .................. | 514/780 |
| 4,874,854 | 10/1989 | Colegrove et al. .................. | 536/114 |

FOREIGN PATENT DOCUMENTS

| | | |
|---|---|---|
| 0077680 | 4/1983 | European Pat. Off. . |
| 227494 | 7/1987 | European Pat. Off. . |
| 2588189 | 4/1987 | France . |
| 2164658 | 3/1986 | United Kingdom . |

Primary Examiner—Ronald W. Griffin
Attorney, Agent, or Firm—W. H. Nicholson; M. C. Sudol, Jr.

[57] ABSTRACT

The present invention concerns a pharmaceutical and/or cosmetic composition designed to be applied on the skin or the mucosae, characterized in that it contains Rhamsan gum.

3 Claims, No Drawings

PHARMACEUTICAL AND/OR COSMETIC COMPOSITION FOR LOCAL USE CONTAINING RHAMSAN GUM

The present invention relates to a pharmaceutical and/or cosmetic composition for topical use, the formulation of which permits a slow and gradual release of the active principle on the skin or the mucosae, in particular on the conjunctiva.

One of the main penetration routes for ophthalmic compositions is the cornea. The cornea is, in effect, a fibrous membrane which is non-vascularized but permeable to all water-soluble substances.

This membrane is protected by a mucosa, the conjunctiva, on which the ophthalmic compositions are applied.

Various known processes enable the contact time between the eye lotion and the conjunctiva to be prolonged. It has been known for a long time that the act of depositing drops of eye lotion in the outer corner of the eye enables lachrymal drainage to be delayed. It is also known to use viscous solutions, gels, eye ointments or even occular implants for the purpose of prolonging the residence time of the eye lotion in the eye.

To increase the contact time between the ophthalmic compositions and the conjunctiva, the use of special adjuvants, such as gums or polymers, is also recommended.

For example, C. Rosenblum et al. (Arch Ophthal, 77: 234-237, 1967) describes the use of hydroxyethylcellulose for increasing the systemic absorption of dexamethasone by the eye tissues.

Y.F. Maichuk (Am. J. Ophthal, 74: 694, 1972) shows that the use of polyvinyl alcohol enhances the pharmacological response to medicinal products such as erythrocin propionate and sulphapyridazine sodium. Similarly, guar gum has been shown to increase the absorption of tropicamide via the cornea (Lee et al., J. Pharm. Sci. 63: 721, 1974).

The use of combinations between gum and polymer is also described, and in particular by way of a bactericidal cleaning agent, a lubricant and a wetting agent. Thus, for example, German Pat. No. 2,051,369 describes a solution containing polyethylene glycol, poly(ethylene oxide) and an ophthalmic medicinal product.

Similarly, British Pat. No. 1,337,105 describes a different combination of polymers designed to be used in solutions for cleaning the eyes and containing hydroxyethylcellulose and polyvinyl alcohol.

Another example relates to British Pat. No. 1,340,518, which describes ophthalmic compositions containing an ophthalmic medicinal product, a polyalkylene glycol, a cellulose derivative or a mixture of these derivatives with, where appropriate, polyvinylpyrrolidone.

Similarly, U.S. Pat. Nos. 3,944,427 and 3,700,451 describe compositions which are capable of gelation and in gel form, containing agar, xanthan gum and carob gum in a liquid medium which is usable by way of a vehicle in therapeutic solutions. U.S. Pat. No. 4,136,177 also describes the use of xanthan gum in ophthalmic compositions.

Xanthan gum, however, has the disadvantage of being partially degraded under the effect of heat; with an instability of this kind, it is difficult to achieve compatibility with sterilization in the autoclave, which is required in the formulation of eye lotions.

The present invention relates to a pharmaceutical and/or cosmetic composition designed to be applied on the skin or the mucosae, characterized in that it contains Rhamsan gum.

It has been shown, in effect, altogether unexpectedly, that Rhamsan gum prolongs the period of action of pharmaceutical and/or cosmetic compositions designed to be applied on the skin or the mucosae.

In the particular case of ophthalmic compositions, Rhamsan gum enables the residence time of the said compositions in the pre-corneal area, that is to say at the conjunctival level, to be very substantially prolonged.

The bioavailability of the medicinal product therein is consequently greatly improved, thereby permitting a substantial parallel decrease in the side effects.

Futhermore, Rhamsan gum shows exceptional thermal stability; this stability enables the compositions according to the invention to be sterilized in the autoclave.

Rhamsan gum endows the compositions according to the invention with a more or less viscous consistency, or even a gel consistency, a consistency of this kind depending on the concentration of this polymer in the said compositions.

Rhamsan gum is an extracellular anionic heteropolysaccharide produced by the organism ATCC 31961

This polymer is manufactured by Kelco Co. It is also known under the code names S-194 or KI A 112. It is described in U.S. Pat. No. 4,401,760.

Its structure comprises a linear tetrasaccharide skeleton bearing a disaccharide side chain, and it may be represented in the following manner:

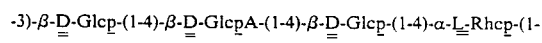

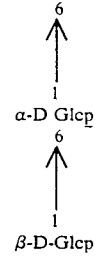

The Rhamsan gum used according to the present invention is preferably of clarified grade.

The compositions according to the present invention preferably contain Rhamsan gum in the proportion of between 0.05% and 3% (w/w).

The viscosity of these compositions increases with the percentage of gum to become a gel at the strongest concentrations.

The preferred compositions according to the present invention are ophthalmic compositions.

These ophthalmic compositions can be used in very varied fields of application, and in particular for maintaining satisfactory hydration of the eye (treatment of the dry eye syndrome).

It appears that the ophthalmic compositions according to the invention are especially suitable for the administration of any pharmacologically active substance for curative or diagnostic purposes.

The present invention relates more especially to ophthalmic compositions containing 0.001% to 5% (w/w) of at least one pharmacologically active substance.

By pharmacologically active substance, there are understood one or more medicinal substances.

Water-soluble substances are preferably chosen, but lipid-soluble active principles can also be appropriate to compositions according to the present invention, in particular in the form of suspensions or emulsions in the aqueous polysaccharide solutions of the present invention.

Among water-soluble substances, some are more readily solubilized in the aqueous polysaccharide solutions of the present invention, and their use is hence especially preferred.

Although the compositions of the present invention are principally ophthalmic compositions, the present invention relates to all other pharmaceutical compositions containing Rhamsan gun.

Thus, the pharmaceutical systems for delivery of an active principle according to the invention can be used internally and/or externally, and in particular topically, orally, nasally and buccally.

Other advantages and characteristics will emerge on reading the following examples:

EXAMPLE 1

Composition for the delivery of a carbonic anhydrase inhibitor

|  | per gram |
| --- | --- |
| L-651,465-OOX | 20.6 mg |
| Rhamsan | 6.00 mg |
| Sodium acetate 3H$_2$O | 8.98 mg |
| Sodium edetate | 0.50 mg |
| Benzalkonium chloride | 0.011 mg |
| Hydrochloric acid (0.1 N solution) | 4.760 mg |
| Water for injection | qs 1 g |

Concentrations of L-650,719 (active metabolite) are measured in the aqueous humour of unanaesthetized albino rats following single instillations of 50 μl of 2% strength L-651,465 formulations containing 0.6% of Rhamsan gum and 0.5% of hydroxyethylcellulose QP 52000H, which is a widely used viscosity-enhancing agent.

The results given below show that the bioavailability of the medicinal product is significantly increased by using the Rhamsan formulation.

LEVELS OF L-650,719 IN THE AQUEOUS HUMOUR
INDUCED AFTER INSTILLATIONS OF 50 μl OF 2%
STRENGTH L-651,465 FORMULATIONS
The results are expressd in mcg of 650,719/ml of aqueous
humour ± standard deviation.

| SAMPLING TIME FORMULATION | 30 min | 1 h | 2 h | 3 h | 4 h |
| --- | --- | --- | --- | --- | --- |
| 0.5% hydroxy-ethylcellulose | 3.29 ± 0.91 | 4.19 ± 1.93 | 1.91 ± 0.36 | 0.57 ± 0.24 | 0.18 ± 0.15 |
| 0.6% Rhamsan | 3.64 ± 1.60 | 3.48 ± 1.36 | 4.95 ± 1.22 | 3.38 ± 2.37 | 0.49 ± 0.39 |

EXAMPLE 2

| Composition containing timolol in solution | |
| --- | --- |
| Timolol (maleate) | 0.250 g |
| Rhamsan gum | 0.600 g |
| Monobasic sodium phosphate | 0.721 g |
| Dibasic sodium phosphate | 1.158 g |
| Benzalkonium chloride | 0.010 g |
| Distilled water | qs 100 ml |

EXAMPLE 3

| Composition for delivery of timolol in a gel | |
| --- | --- |
| Timolol (maleate) | 0.250 g |
| Rhamsan gum | 3.000 g |
| Monobasic sodium phosphate | 0.721 g |
| Dibasic sodium phosphate | 1.158 g |
| Benzalkonium chloride | 0.010 g |
| Distilled water | qs 100 g |

EXAMPLE 4

| Composition containing Norfloxacine in the form of a gel | |
| --- | --- |
| Norfloxacine | 0.300 g |
| Rhamsan | 3.000 g |
| Disodium EDTA | 0.010 g |
| Benzalkonium chloride | 0.0025 g |
| Sodium acetate trihydrate | 0.0272 g |
| Sodium chloride | 0.742 g |
| Hydrochloric acid to adjust the pH to 5.2-6 | |
| Distilled water | qs 100 g |

The above examples, and in particular the results which appear in the table, clearly demonstrate the prolonged pharmacological effects of the compositions containing Rhamsan gum according to the invention.

I claim:

1. An ophthalmic composition comprising Rhamsan gum and at least one ophthalmic pharmacologically active substance.

2. An ophthalmic composition according to claim 1, which contains Rhamsan gum in the proportion of between 0.05% and 3% (w/w).

3. A composition according to claim 2 which contains 0.001% to 5% (w/w) of the ophthalmic pharmacologically active substance or substances.

* * * * *